(12) United States Patent
Taton

(10) Patent No.: US 10,744,233 B2
(45) Date of Patent: Aug. 18, 2020

(54) CRYSTALLIZATION INHIBITOR COMPOSITIONS FOR IMPLANTABLE UROLOGICAL DEVICES

(71) Applicant: Innovative Surface Technologies, Inc., St. Paul, MN (US)

(72) Inventor: Kristin Taton, Little Canada, MN (US)

(73) Assignee: Innovative Surface Technologies, Inc., St. Paul, MN (US)

( * ) Notice: Subject to any disclaimer, the term of this patent is extended or adjusted under 35 U.S.C. 154(b) by 0 days.

(21) Appl. No.: 16/079,218

(22) PCT Filed: Feb. 24, 2017

(86) PCT No.: PCT/US2017/019498
§ 371 (c)(1),
(2) Date: Aug. 23, 2018

(87) PCT Pub. No.: WO2017/147521
PCT Pub. Date: Aug. 31, 2017

(65) Prior Publication Data
US 2019/0091375 A1    Mar. 28, 2019

Related U.S. Application Data

(60) Provisional application No. 62/299,035, filed on Feb. 24, 2016.

(51) Int. Cl.
| | | |
|---|---|---|
| *A61L 29/16* | (2006.01) | |
| *A61K 31/194* | (2006.01) | |
| *A61L 29/06* | (2006.01) | |
| *A61L 29/08* | (2006.01) | |
| *A61L 31/16* | (2006.01) | |
| *A61L 31/06* | (2006.01) | |
| *A61K 9/00* | (2006.01) | |
| *A61K 9/50* | (2006.01) | |
| *A61L 31/10* | (2006.01) | |
| *A61K 38/19* | (2006.01) | |
| *A61K 31/765* | (2006.01) | |
| *A61K 38/18* | (2006.01) | |
| *A61L 29/04* | (2006.01) | |
| *A61L 29/14* | (2006.01) | |

(52) U.S. Cl.
CPC ............ *A61L 29/16* (2013.01); *A61K 9/0034* (2013.01); *A61K 9/0092* (2013.01); *A61K 9/5031* (2013.01); *A61K 31/194* (2013.01); *A61K 31/765* (2013.01); *A61K 38/1875* (2013.01); *A61K 38/19* (2013.01); *A61L 29/042* (2013.01); *A61L 29/06* (2013.01); *A61L 29/085* (2013.01); *A61L 29/145* (2013.01); *A61L 29/148* (2013.01); *A61L 31/06* (2013.01); *A61L 31/10* (2013.01); *A61L 31/16* (2013.01); *A61L 2300/216* (2013.01); *A61L 2300/252* (2013.01); *A61L 2300/404* (2013.01); *A61L 2300/604* (2013.01); *A61L 2300/606* (2013.01); *A61L 2300/608* (2013.01); *A61L 2400/02* (2013.01)

(58) Field of Classification Search
CPC ........ A61L 29/00; A61L 29/005; A61L 29/08; A61L 29/12; A61L 29/042
See application file for complete search history.

(56) References Cited

U.S. PATENT DOCUMENTS

| | | |
|---|---|---|
| 3,699,080 A | 10/1972 | Sayigh et al. |
| 3,794,736 A | 2/1974 | Abbott et al. |
| 4,981,988 A | 1/1991 | Ichinohe et al. |
| 5,002,582 A | 3/1991 | Guire et al. |
| 5,271,945 A | 12/1993 | Yoshioka et al. |
| 5,512,329 A | 4/1996 | Guire et al. |
| 5,554,147 A | 9/1996 | Batich et al. |
| 5,877,243 A | 3/1999 | Sarangapani |
| 5,888,656 A | 3/1999 | Suzuki et al. |
| 5,980,972 A | 11/1999 | Ding |
| 5,997,517 A | 12/1999 | Whitbourne |
| 6,099,562 A | 8/2000 | Ding et al. |
| 6,120,536 A | 9/2000 | Ding et al. |
| 6,254,634 B1 | 7/2001 | Anderson et al. |
| 6,465,525 B1 | 10/2002 | Guire et al. |
| 6,773,888 B2 | 8/2004 | Li et al. |
| 6,808,738 B2 | 10/2004 | Ditizio et al. |

(Continued)

FOREIGN PATENT DOCUMENTS

| | | |
|---|---|---|
| WO | 89/05671 A1 | 6/1989 |
| WO | 2002058753 A2 | 8/2002 |

(Continued)

OTHER PUBLICATIONS

Keana, John F.W. et al., "New Reagents for Photoaffinity Labeling: Synthesis and Photolysis of Functionalized Perfluorophenyl Azides," J. Org. Chem. 55:3640-3647 (1990).

(Continued)

*Primary Examiner* — Micah Paul Young
(74) *Attorney, Agent, or Firm* — Karrie Gemignani Weaver; Weaver Legal and Consulting LLC

(57) ABSTRACT

Inventive concepts relate generally to the field of implantable urological devices, and more particularly to compositions that inhibit crystallization of urine components. Described are implantable urological devices including a surface and a crystallization inhibitor composition, the crystallization inhibitor composition including: (a) an inhibitor of urine component crystallization in combination with a biodegradable polymer, or a polyalkene homopolymer or copolymer, or (b) a biodegradable polymer that includes an inhibitor of urine component crystallization, wherein the crystallization inhibitor composition provides controlled release of the inhibitor of urine component crystallization from the surface of the device into a subject. Methods of making the implantable urological devices are also described.

22 Claims, 5 Drawing Sheets

(56) References Cited

U.S. PATENT DOCUMENTS

| | | |
|---|---|---|
| 7,544,673 B2 | 6/2009 | DeWitt et al. |
| 7,772,393 B2 | 8/2010 | Guire et al. |
| 8,034,369 B2 | 10/2011 | Anderson et al. |
| 8,142,836 B2 | 3/2012 | Chappa |
| 8,361,052 B2 | 1/2013 | Tremblay |
| 8,404,264 B2 * | 3/2013 | Ameer .................. A61L 27/16 424/422 |
| 8,496,954 B2 | 7/2013 | Chappa et al. |
| 8,679,454 B2 | 3/2014 | Guire et al. |
| 2004/0220665 A1 | 11/2004 | Hossainy et al. |
| 2005/0100577 A1 | 5/2005 | Parker et al. |
| 2006/0069068 A1 | 3/2006 | Kajander et al. |
| 2006/0127438 A1 | 6/2006 | Hunter et al. |
| 2007/0054127 A1 | 3/2007 | Hergenrother et al. |
| 2007/0208420 A1 | 9/2007 | Ameer et al. |
| 2007/0275027 A1 | 11/2007 | Wen et al. |
| 2008/0208334 A1 | 8/2008 | Jinkerson et al. |
| 2008/0312315 A1 | 12/2008 | Daniloff et al. |
| 2009/0092843 A1 | 4/2009 | Arlt et al. |
| 2011/0159072 A1 | 6/2011 | Missling et al. |
| 2011/0223212 A1 | 9/2011 | Taton et al. |
| 2011/0238163 A1 * | 9/2011 | Andrews ................ A61L 29/14 623/1.46 |
| 2012/0100187 A1 | 4/2012 | Chappa et al. |
| 2012/0258313 A1 | 10/2012 | Wen et al. |
| 2012/0302950 A1 | 11/2012 | Landsman et al. |
| 2013/0177504 A1 * | 7/2013 | Macoviak ............... A61K 8/29 424/10.3 |
| 2014/0178447 A1 | 6/2014 | Modak et al. |
| 2014/0214175 A1 | 7/2014 | Barron et al. |

FOREIGN PATENT DOCUMENTS

| | | |
|---|---|---|
| WO | 2004014447 A1 | 2/2004 |
| WO | 2004043510 A1 | 5/2004 |
| WO | 2005035637 A1 | 4/2005 |
| WO | 2005046521 A1 | 5/2005 |
| WO | 2005099786 A1 | 10/2005 |
| WO | 2006036801 A2 | 4/2006 |
| WO | 2007056338 A2 | 5/2007 |
| WO | 2007097614 A1 | 8/2007 |
| WO | 2008103668 A2 | 8/2008 |
| WO | 2013006947 A1 | 1/2013 |
| WO | 2014176545 A1 | 10/2014 |

OTHER PUBLICATIONS

Werner et al., "Maleic Anhydride Copolymers—A Versatile Platform for Molecular Biosurface Engineering," Biomacromolecules, 2003, 4, pp. 1072-1079.

Wu, et al., "Viscosity-Molecular Weight Relationship for Aminopropyl-Terminated poly(dimethylsiloxane)," Journal of pplied Polymer Science, 2001, 80, pp. 975-978.

International Search Report and Written Opinion for corresponding International Application No. PCT/US2017/019498, dated May 18, 2017 (9 pages).

Supplementary European Search Report for corresponding European Application No. EP 17 75 7374, dated Oct. 2, 2019 (4 pages).

* cited by examiner

CRYSTALLIZATION INHIBITOR COMPOSITIONS FOR IMPLANTABLE UROLOGICAL DEVICES

CROSS-REFERENCE TO RELATED APPLICATIONS

This application is a Section 371 National Stage Application of International Application No. PCT/US2017/019498, filed Feb. 24, 2017 and published as WO 2017/147521 on Aug. 31, 2017, which claims priority from U.S. Provisional Application No. 62/299,035, filed Feb. 24, 2016, the contents of which are incorporated herein in their entirety for all purposes.

This invention was made with government support under Grant No. 1R43DK097934-01, awarded by the National Institutes of Health (NIH), the National Institute of Diabetes and Digestive and Kidney Diseases (NIDDK). The government has certain rights in the invention.

FIELD

The present invention relates generally to medical devices, and more particularly to implantable urological devices that release one or more crystallization inhibitors.

BACKGROUND

Medical devices, for example urological medical devices such as urinary "Foley" catheters, urethral stents and ureteral stents, among others, have been useful for treating a variety of medical conditions. Ureteral stents help maintain urine flow from the kidneys, through the ureter, to the bladder following many common urological procedures. It is estimated that over 135,000 people were hospitalized for kidney stones and over 17,000 kidney transplants took place in 2007—both procedures frequently necessitating ureteral stents. Such stents facilitate kidney stone/fragment passage, act as scaffolds for healing in cases of ureter laceration or reconstructive surgery, prevent ureteral strictures, and facilitate drainage following kidney transplant or during malignancies. While some of these stents are used temporarily, others are left in the body for weeks or months. During this time, the stent becomes both encrusted with crystalline material of calcium and magnesium, and covered with a bacterial biofilm that may increase pH. These two effects often work together. Bacteria in the biofilm can raise urine pH, which in turn, precipitates calcium salts onto the stent. However, they also work distinctly—even eliminating bacteria does not necessarily reduce encrustation.

Regardless of the mechanisms of encrustation and biofilm formation, there is a need for the development of implantable/insertable devices that are capable of preventing, reducing and/or treating encrustation and biofilm formation caused by the implantation or insertion of such devices into a patient's body.

SUMMARY

Methods and compositions to decrease or inhibit encrustation of urological devices have been developed. In accordance with inventive principals, crystallization inhibitor compositions, provided as coatings or otherwise associated with an implantable urological device, contain and elute inhibitors of salt crystallization that stimulate encrustation of the device surface.

In some aspects, inventive concepts provide an implantable urological device comprising a surface and a crystallization inhibitor composition, the crystallization inhibitor composition comprising:
 (a) an inhibitor of urine component crystallization in combination with, or included in, a biodegradable polymer, or
 (b) an inhibitor of urine component crystallization and a hydrophobic polymer,
wherein the crystallization inhibitor composition provides controlled release of the inhibitor of urine component crystallization from the surface of the device into a subject.

According to inventive concepts, exemplary inhibitors of urine component crystallization include, but are not limited to, citric acid and osteopontin. These exemplary inhibitors have been formulated and compared for slow, continuous, controlled, and sustained release from the surface of a substrate of a medical device. These two compounds are each known to inhibit crystallization of multiple forms of salts in urinary fluids including, for example, calcium oxalate, calcium phosphate, and calcium carbonate. Urinary salt nucleation can lead to aggregation and ultimately encrustation of an implanted urological device. Often encrustation occurs via crystal formation of the salts of calcium or magnesium. Further, a microbial biofilm is frequently present on the surface of an implanted device, such as stent. Antimicrobial or anti-infection agents can also be provided from the composition in accordance with inventive concepts, to reduce or inhibit microbial stimulated biofilm formation.

In some aspects, a medical device, comprising a surface and a crystallization inhibitor composition disposed on the surface is provided. The crystallization inhibitor composition controllably releases one or more inhibitors of urine component crystallization in a sustained manner from on or within the surface in an amount effective to cause a reduction in encrustation and/or biofilm formation on or near the medical device. The inhibitor of urine component crystallization may comprise citric acid or osteopontin, for example.

In some aspects, the biodegradable polymer of the crystallization inhibitor composition can comprise a biodegradable polymer, such as a biodegradable polyester. Biodegradable polymers can be of synthetic or natural origin. In some embodiments, the biodegradable polymer can comprise a poly(diol-citrate) copolymer. Optionally, biodegradable polymer can comprise poly(DL-lactide-co-glycolide), poly(lactic acid), poly(L-lactic acid), polycaprolactone, poly(hydroxybutyrate) (PHB), poly(glycolic acid) (PGA), natural biodegradable polymers, copolymers and mixtures of any of these.

Inventive concepts include embodiments wherein hydrophobic polymer comprises a polyalkene homopolymer or copolymer. Illustrative polyalkene polymer includes polyisobutylene.

Crystallization inhibitor compositions can be provided as a coating associated with the implantable urological device surface. Alternatively, crystallization inhibitor compositions can be provided in reservoirs or other cavities in or near the device surface or internal lumen. When provided as a coating, crystallization inhibitor compositions can be provided directly on the device surface, or optionally can include a primer layer between it and the device surface. Optionally, a topcoat or overcoat layer can be provided to the crystallization inhibitor composition. In embodiments containing multiple layers, the particular composition of each coating layer can be the same or different, as desired.

In some aspects, crystallization inhibitor compositions can comprise the inhibitor of urine component crystallization provided in a microparticle of biodegradable polymer. Inventive crystallization inhibitor compositions can include one or more distinct microparticle populations, wherein each population can include a selected polymer, inhibitor of urine component crystallization, and optional components such as antimicrobial agents, additives, binders, and the like.

Inventive concepts also contemplate implantable urological devices comprising a surface and a multilayer coating on the surface, the coating comprising:
(a) a primer coating layer;
(b) a citric acid coating layer; and
(c) a polymeric topcoat layer disposed on the citric acid coating layer,
wherein the multilayer coating provides controlled release of the citric acid from the surface of the device into a subject.

Further inventive concepts include implantable urological devices comprising a surface and a multilayer coating on the surface, the coating comprising:
(a) a citric acid coating layer; and
(b) a polymeric topcoat layer disposed on the citric acid coating layer,
wherein the multilayer coating provides controlled release of the citric acid from the surface of the device into a subject.

According to inventive concepts, coatings containing the crystallization inhibitor compositions demonstrate a durability.

In some aspects, methods are described that comprise steps of:
(a) providing a crystallization inhibitor composition to a surface of an implantable urological device, thereby providing a crystallization inhibitor coating to the surface, the crystallization inhibitor composition comprising a crystallization inhibitor in combination with a biodegradable polymer or a polyalkene copolymer that includes an inhibitor of urine component crystallization; and
(b) applying a polymer coating layer to the crystallization inhibitor coating.

In some aspects, medical devices include ureteral stents, urinary catheters, urethral stents, ureteral catheters, urinary drainage systems, and other implantable urological medical devices.

DETAILED DESCRIPTION

Figure 1:
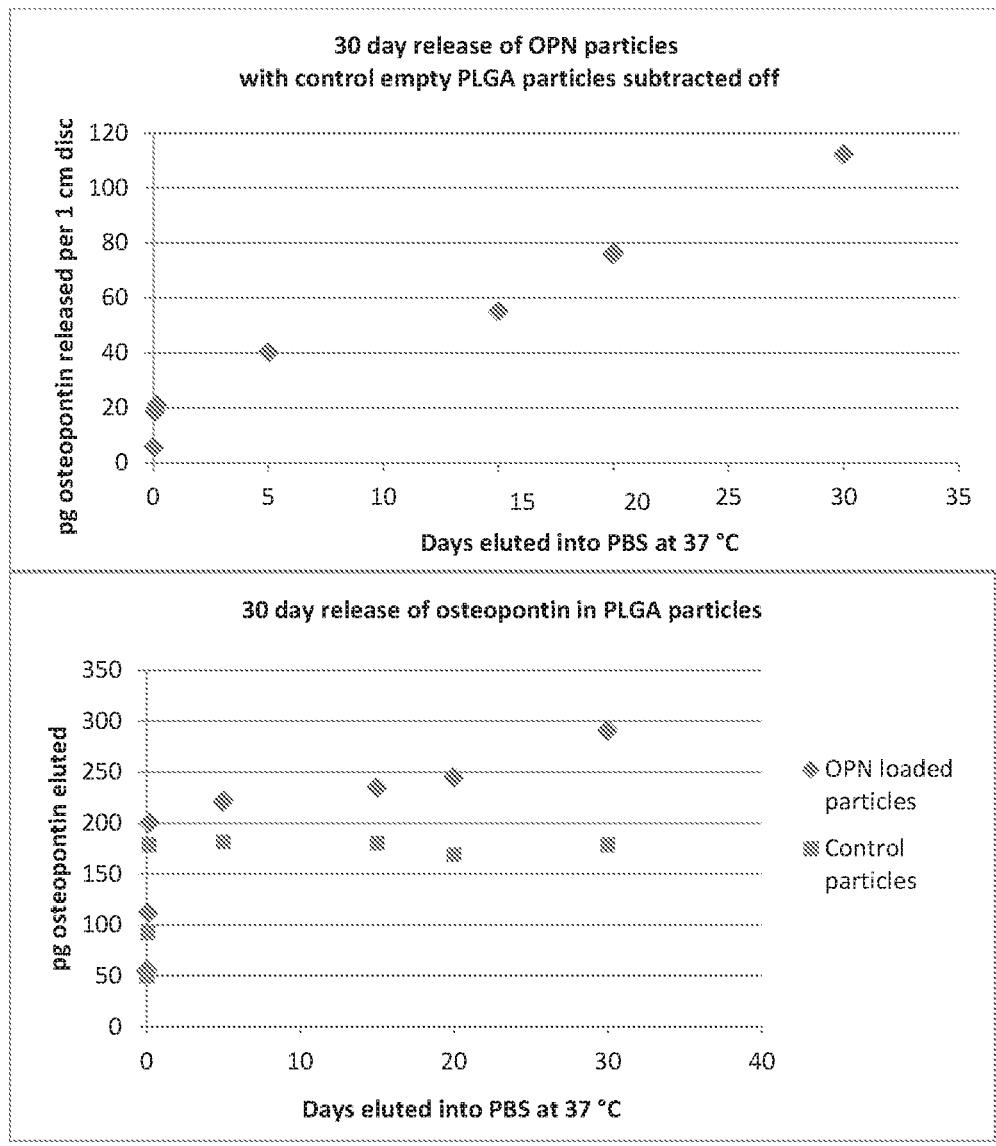
FIG. 1 illustrates crystallization inhibitor release from hydrogel coatings on discs over 30 days at 37° C. into PBS. A) Crystallization inhibitor release with control empty microparticles subtracted off, B) both sets of data.

A more complete understanding of inventive concepts is available by reference to the following detailed description of numerous aspects and embodiments. The detailed description which follows is intended to illustrate but not limit the embodiments.

The medical devices of the embodiment are urological medical devices, including any medical device that is suitable for placement in the urinary system of a subject, including the kidneys (e.g., in the renal calyx, renal pelvis, etc.), as well as the urinary tract, including ureters, urinary bladder and urethra.

In a general sense, urological medical devices are provided which comprise a surface and a crystallization inhibitor composition, wherein the crystallization inhibitor composition includes an inhibitor of urine component crystallization in a manner by which the inhibitor can be released from the device in a controlled and sustained way. Examples of such substrates include urinary (e.g., Foley) catheters and portions thereof, ureteral stents and portions thereof, urethral stents and portions thereof, ureteral catheters and portions thereof.

Renal tubular fluid and urine can become supersaturated with respect to calcium and/or magnesium salts. When there is a high concentration of calcium and/or magnesium salts, crystal nucleation, growth, aggregation and attachment to renal tissues and/or an implanted urological device may occur. By controllably releasing inhibitors of urine component crystallization, inventive devices and methods can decrease or inhibit encrustation of implantable urological devices. As discussed herein, an inhibitor of urine component crystallization can act to inhibit and/or decrease one or more of crystal nucleation, growth, aggregation and/or attachment. Further, because the inhibitors of urine component crystallization are eluted from the device, inventive devices and methods can inhibit or decrease crystallization not only on the device, but also in solution (renal tubular fluid and/or urine). This can provide significant benefits to reduce, minimize and/or prevent device encrustation.

Two generally known inhibitors—citric acid and osteopontin were formulated and compared for slow, continuous and sustained release from the surface. These two compounds are each known to inhibit crystallization of multiple forms of encrustation including, for example, calcium oxalate, calcium phosphate, and calcium carbonate. Often encrustation via crystal formation of the salts of calcium or magnesium, can be from 10 microns in depth to visible encrustation. At 3 months, there can be an average of 17 micron encrustation on 86% of the ureteral stent surface area. Further, a microbial biofilm is frequently present on the surface of the stent.

Sustained release of inhibitors of urine component crystallization can advantageously allow the implantable urological device (such as a stent or catheter) to continuously have inhibitor on the surface of the substrate as well as in nearby mammalian solution or tissue, potentially affecting the surrounding milieu to inhibit crystal formation, aggregation, and decrease pH (for citric acid). Citric acid is known to inhibit salt formation from magnesium and calcium. Citrate ions ($C_3H_5(COO)_3^{3-}$) coordinate strongly to calcium and magnesium salts leading to inhibition or suppression of crystal formation. Further, citrate ions can decrease pH on the surface of the substrate of the medical device as well as in the immediately surrounding tissues.

Inhibitors of urine component crystallization are compounds that decrease rates of crystallization of salt forming compounds from an aqueous solution. Examples of salt forming compounds are calcium and magnesium salts such as oxalates, carbonates, phosphates, urates and others. These and other salts from urine solutions are targets of the crystallization inhibitors of the embodiments. Not being bound by theory, the crystallization inhibitor is thought to delay or impede nucleation or inhibit crystal grown by binding to a specific crystal face, such as the <1,0,0> face of calcium oxalate monohydrate by citric acid, which inhibits further crystal growth. Crystal inhibitors may be small molecules (molecular weight <1000) or macromolecules (molecular weight >1000), such as proteins or polymers.

The use of other inhibitors of urine component crystallization are contemplated, particularly inhibitors that act to decrease, minimize or prevent formation of calcium or magnesium salts. Such inhibitors of urine component crystallization can be selected based upon such characteristics as, for example, biocompatibility with mammalian tissue, stability in a coating layer and controlled released from the surface of the medical device substrate.

"Inhibitors of urine component crystallization" (sometimes referred to herein as "crystallization inhibitors" or "inhibitors"), as the term is used in this application, may be hydrophilic or hydrophobic, may be charged or neutral, and can include metal ions or charged hydrocarbons. Examples of inhibitors of urine component crystallization may include osteopontin, citric acid and other citrates, stearic acid, diacids, phytates (phytic acid), methylxanthines, pyrophosphates, phosphates, phosphonates, chondroitin sulfate, glycosaminoglycans, saponin, albumin, transferrin, cellulose hydroxypropyl methylcellulose, carboxymethylcellulose, and other cellulose derivatives, polyvinylpyrrolidone, polyacrylamides, polyethyleneglycols, pentaerythritol, methylpyrrolidone, pyrollidone, piracetam, polyvinylalcohol, polymethacrylates, polyacrylates and others.

In an embodiment, these novel crystallization inhibitor compositions are coatings comprising citric acid that are stable to model insertion conditions, such as durability (a frictional force of at least 100 g), and that elute over at least a 7, 14, 28, 60, or 90, day period.

In an embodiment, these novel compositions are coatings comprising osteopontin that are stable to model insertion conditions, such as durability (a frictional force of 100 g), and that elute over at least a 7, 14, 28, 60, or 90, day period.

In an embodiment, these novel compositions are coatings comprising an inhibitor of urine component crystallization, wherein the coating reduces encrustation in vitro by at least 20, 30, 40, 50, or 60% compared with an uncoated surface on a substrate composed of a common material used for fabrication of implantable medical devices, such as for example, polyurethane.

Citric Acid

At room temperature, citric acid is a white hygroscopic crystalline powder. It can exist either in an anhydrous (water-free) form or as a monohydrate. The anhydrous form crystallizes from hot water, while the monohydrate forms when citric acid is crystallized from cold water. The monohydrate can be converted to the anhydrous form by heating above 78° C. Citric acid also dissolves in absolute (anhydrous) ethanol (76 parts of citric acid per 100 parts of ethanol) at 15° C.

In chemical structure, citric acid shares the properties of other carboxylic acids. When heated above 175° C., it decomposes through the loss of carbon dioxide and water (see decarboxylation).

Citric acid is a slightly stronger acid than typical carboxylic acids because the anion can be stabilized by intramolecular hydrogen-bonding from other protic groups on citric acid.

Osteopontin

Osteopontin (OPN), also known as bone sialoprotein I (BSP-1 or BNSP), early T-lymphocyte activation (ETA-1), secreted phosphoprotein 1 (SPP1), 2ar and *Rickettsia* resistance (Ric), is a protein that in humans is encoded by the SPP1 gene (secreted phosphoprotein 1). The murine ortholog is Spp1. Osteopontin is a SIBLING (glycoprotein) that was first identified in 1986 Synonyms for this protein include sialoprotein I and 44K BPP (bone phosphoprotein).

The gene has 7 exons spans 5 kilobases in length and in humans it is located on the long arm of chromosome 4 region 22 (4q1322.1). The protein is composed of approximately 300 amino acids residues and has approximately 30 carbohydrate residues attached including 10 sialic acid residues, which are attached to the protein during post-translational modification in the Golgi apparatus. The protein is rich in acidic residues: 30-36% are either aspartic or glutamic acid.

In various embodiments, upon implantation or insertion of a urological device into a mammalian subject's urinary system, the medical device releases the inhibitor of urine component crystallization in an amount effective to suppress or inhibit encrustation on at least portions of the surface of the medical device. In an embodiment, this device is a ureteral stent or urethral stent. The amount effective for the crystallization inhibitor dosage can be 0.01, 0.02, 0.03, 0.04, 0.05, 0.06, 0.07, 0.08, 0.09, or 0.10, 0.5, 5, 10, 15, 20, 25, 30, 35, 40, 45, 50 wt. %, based on the total composition, of citric acid or osteopontin, for example.

Without wishing to be bound by theory, it is believed that, by releasing citric acid or osteopontin at and near the medical device surface of its substrate, the formation of crystals of the salts of magnesium and calcium are thereby prevented or delayed from forming. Furthermore, decreased crystallization reduces the likelihood that microbial-based biofilms will form on the medical devices of the present invention, thereby reducing or eliminating microbial biofilm formation.

Subjects for the devices of the present embodiments (also referred to as patients, hosts, and the like) include mammalian subjects, particularly humans and various warm-blooded animals including pets (for example, dogs, cats, and the like) and livestock (horses, cattle, and the like).

As noted above, urological medical devices are described herein which comprise a surface and a crystallization inhibitor composition, wherein the crystallization inhibitor composition releases an inhibitor of urine component crystallization in a controlled manner (such as sustained release).

Urological devices can be formed from a wide variety of materials such as, for example, polymeric materials, ceramic materials, metallic materials, and combinations of the same. In certain embodiments, urological devices are fabricated from polymers.

Polymers for forming medical devices may be selected from suitable members of the following, among others: polycarboxylic acid polymers and copolymers including polyacrylic acids; acetal polymers and copolymers; acrylate and methacrylate polymers and copolymers (for example, n-butyl methacrylate); cellulosic polymers and copolymers; polyoxymethylene polymers and copolymers; polyimide polymers and copolymers such as polyether block imides, polyamidimides, polyesterimides, and polyetherimides; polysulfone polymers and copolymers including polyarylsulfones and polyethersulfones; polyamide polymers and copolymers including nylon 6,6, nylon 12, polyether-block co-polyamide polymers (for example, Pebax® resins), polycaprolactams and polyacrylamides; polycarbonates; polyacrylonitriles; polyvinylpyrrolidones; polymers and copolymers of vinyl monomers including polyvinyl alcohols, polyvinyl halides such as polyvinyl chlorides, ethylene-vinylacetate copolymers (EVA), polyvinylidene chlorides, polyvinyl ethers such as polyvinyl methyl ethers, vinyl aromatic polymers and copolymers such as polystyrenes, styrene-maleic anhydride copolymers, vinyl aromatic-hydrocarbon copolymers including styrene-butadiene copolymers, styrene-ethylene-butylene copolymers (for example, a polystyrene-polyethylene/butylene-polystyrene (SEBS) copolymer, available as Kraton® G series polymers), styrene-isoprene copolymers (for example, polystyrene-polyisoprene-polystyrene), acrylonitrile-styrene copolymers, acrylonitrile-butadiene-styrene copolymers, styrene-butadiene copolymers and styrene-isobutylene copolymers (for example, polyisobutylene-polystyrene block copolymers such as SIBS), polyvinyl ketones, polyvinylcarbazoles, and polyvinyl esters such as polyvinyl acetates; polybenzimidazoles; ionomers; polyalkyl oxide polymers and copolymers including polyethylene oxides (PEO); polyesters including polyethylene terephthalates, polybutylene terephthalates and aliphatic polyesters such as polymers and copolymers of lactide (which includes lactic acid as well as d-,l- and meso lactide), epsilon-caprolactone, glycolide (including glycolic acid), hydroxybutyrate, hydroxyvalerate, para-dioxanone, trimethylene carbonate (and its alkyl derivatives), 1,4-dioxepan-2-one, 1,5-dioxepan-2-one, and 6,6-dimethyl-1,4-dioxan-2-one (a copolymer of polylactic acid and polycaprolactone is one specific example); polyether polymers and copolymers including polyarylethers such as polyphenylene ethers, polyether ketones, polyether ether ketones; polyphenylene sulfides; polyisocyanates; polyolefin polymers and copolymers, including polyalkylenes such as polypropylenes, polyethylenes (low and high density, low and high molecular weight), polybutylenes (such as polybut-1-ene and polyisobutylene), polyolefin elastomers (e.g., santoprene), ethylene propylene diene monomer (EPDM) rubbers, poly-4-methyl-pen-1-enes, ethylene-alpha-olefin copolymers, ethylene-methyl methacrylate copolymers and ethylene-vinyl acetate copolymers; fluorinated polymers and copolymers, including polytetrafluoroethylenes (PTFE), poly(tetrafluoroethylene-co-hexafluoropropenes) (FEP), modified ethylene-tetrafluoroethylene copolymers (ETFE), and polyvinylidene fluorides (PVDF); silicone polymers and copolymers; polyurethanes; p-xylylene polymers; polyiminocarbonates; copoly(ether-esters) such as polyethylene oxide-polylactic acid copolymers; polyphosphazines; polyalkylene oxalates; polyoxaamides and polyoxaesters (including those containing amines and/or amido groups); polyorthoesters; biopolymers; as well as blends and further copolymers of the above. Biocompatibility with the mammalian subject and durability of the polymer during insertion are illustrative parameters that can be used for selection.

The crystallization inhibitor composition may be in a form of microparticles or coating layers on the surface of the substrate of the medical device or in the substrate of the medical device. Combinations of coating layers and microparticles using the same or different inhibitors of urine component crystallization are also contemplated. These compositions are capable of releasing the inhibitor of urine component crystallization when placed in contact with mammalian body tissue or fluid. The composition can be in the form of a coating formed on the surface of an implantable medical device, or can be independent of a device, such as a composition that is formed in situ containing microparticles.

The crystallization inhibitor composition may include at least one set of microparticles or microspheres. The microparticles can comprise an inhibitor of urine component crystallization, a first polymer, and an optionally a second, third or other polymers with or without inhibitors of urine component crystallization. In some inventive aspects, microparticles can be provided within a polymeric matrix (such as a poly(vinylpyrrolidone) or poly(acrylamide) coating), which allows fluid to penetrate the matrix and contact the microparticles. In some embodiments when a second polymer is present in the microparticle, this second polymer can modulate the release of the inhibitor of urine component crystallization from the matrix. For example, the second polymer can reduce the rate of release of the inhibitor of urine component crystallization from the matrix relative to the rate of release of the inhibitor from a composition having microparticles that do not include the second polymer.

Illustrative polymeric matrix materials include any of the polymers described herein as useful in the crystallization inhibitor composition, such as poly(vinylpyrrolidone); poly(acrylamide); synthetic degradable polymers, such as poly(lactic acid) (PLA), poly(l-lactic acid) (PLLA), polycaprolactone (PCL), poly(D,L-lactide-co-glycolide) (PLGA), polyglycolic acid (PGA), polyorthoesters, poly(dioxanone), poly(anhydrides), poly(trimethylene carbonate), polyphosphazenes, and the like; natural biodegradable polymers such as, for example, polysaccharides such as starch; fibrin; collagen; chitosan; gelatin; hyaluronan; hydrophobic polymers such as polyalkene homopolymers or copolymers, such as polyisobutylene.

The polymeric matrices, either coating or microparticle, can be fabricated so the inhibitor of urine component crystallization is released from the composition with a sustained-release profile. These matrices can avoid a short-term burst of inhibitor and premature depletion of the inhibitor from the matrix. The sustained-release profiles of the coating or microparticle-containing matrices of the present invention allow for release of the inhibitor of urine component crystallization from an implantable medical device, such as for example, a urological device over a longer and more therapeutically useful time period.

In some aspects, the polymers of the crystallization inhibitor composition (whether provided in the form of microparticle, coating, or both) are degradable polymers. In order to reduce the rate of release of inhibitor of urine component crystallization, the microparticles or coating can comprise a second biodegradable polymer that has a rate of degradation that is slower than the first biodegradable polymer. In some cases, the second biodegradable polymer is a biodegradable homopolymer and the first biodegradable polymer is a biodegradable copolymer. Exemplary polymers are synthetic degradable polymers, such as poly(lactic acid) (PLA), poly(l-lactic acid) (PLLA), polycaprolactone (PCL), poly(D,L-lactide-co-glycolide) (PLGA), polyglycolic acid (PGA), polyorthoesters, poly(dioxanone), poly(anhydrides), poly(trimethylene carbonate), polyphosphazenes, and the like; as well as natural biodegradable polymers such as, for example, polysaccharides such as starch; fibrin; collagen; chitosan, gelatin; hyaluronan; and the like.

In some aspects, the microparticles and/or coating can be structured so that a predominant amount of second polymer is in mixture with the inhibitor of urine component crystallization. For example, the microparticles can include a core-shell structure, wherein the core comprises the first polymer in mixture with the inhibitor, and the shell comprises the second polymer. In some aspects the composition comprises polymer and reacted groups. The reacted groups can covalently couple the polymeric material together, or covalently couple the polymeric material to a surface of a medical device in the case of a coating or microparticle, or both.

In some aspects, the crystallization inhibitor composition is formed of hydrophilic polymers. Exemplary polymers include poly(vinylpyrrolidone) and poly(acrylamide). In some cases, the reacted groups of the matrix are photoreactive groups that have been activated to bond the polymer to a device surface and/or another polymer. In some cases, the reacted groups are latent reactive groups that have been activated and that are pendent from the polymer.

"Photoreactive groups" or "photo-activatable reactive chemical groups" are chemically inert compounds that become reactive when exposed to ultraviolet or visible light. When exposed to an appropriate energy source, a photoreactive species undergoes a transformation from an inactive state (ground state) to a reactive intermediate capable of forming covalent bonds with appropriate materials. Useful photoreactive groups are described, for example, in U.S. Pat. No. 5,002,582 (Guire et al.) and U.S. Pat. No. 7,772,393 B2 (Guire et al.).

In some aspects, the microparticles have a size of less than 10, 20, 30, 40, 50, 100, or 200 µm. In some aspects, the polymer matrix is in the form of a coating on an implantable medical device. The coating can include microparticles immobilized in the matrix, the microparticle comprising a crystallization inhibitor, a polymer, and optionally a second polymer, wherein the second polymer modulates release of the crystallization inhibitor from the coating. In some aspects, the coating is formed of a matrix of polymeric material comprising reacted groups (which form the coating) and microparticles immobilized in the polymeric matrix. The coating has properties, such as biocompatibility and durability that are suitable for use within a subject.

The microparticle composition, in conjunction with the polymeric matrix, provides a particularly effective mechanism for the sustained delivery of inhibitors of urine component crystallization, as well as biolfilm inhibitors such as antimicrobial agents. For example, the present matrix can also be used to deliver large crystallization inhibitors, such as polypeptides, polysaccharides, or polynucleotides, from the surface of the device.

Therefore, in some aspects, the microparticles immobilized in the matrix comprise an inhibitor of urine component crystallization such as, for example, citric acid or osteopontin having a molecular weight of 1,000 Da or greater. In some aspects, the device has an inhibitor release profile wherein not more than 50% of the inhibitor of urine component crystallization present in the coating is released within a period of 24 hours. In more specific aspects, the device has an inhibitor release profile wherein not more than 50% of the inhibitor of urine component crystallization present in the coating is released within a period of 1 to 14 days, 1 to 29 days, 2 to 18 days, 3 to 11 days, or 4 to 8 days.

In an embodiment, inventive concepts provide a method comprising steps of:

a) providing a crystallization inhibitor composition to a surface of an implantable urological device, thereby providing a crystallization inhibitor coating to the surface, the crystallization inhibitor composition comprising (i) an inhibitor of urine component crystallization in combination with, or included in, a biodegradable polymer, or (ii) an inhibitor of urine component crystallization and a hydrophobic polymer; and (b) applying a polymer coating layer to the crystallization inhibitor coating.

In some aspects, the polymer of step (b) comprises a polyalkene. Optionally, the method can further comprises a step of providing a primer coating layer prior to step (a). In accordance with some inventive aspects, the step of providing a primer coating layer comprises providing photo-poly (octadecene-alt-maleic anhydride) silane to the surface of the implantable urological device.

The crystallization inhibitor composition can comprise a polymeric material and at least one set of microparticles, the microparticles comprising an inhibitor of urine component crystallization, a first polymer, and an optional second polymer, wherein the second polymer modulates release of the inhibitor from the crystallization inhibitor composition. The composition is then treated to provide a matrix comprising immobilized microparticles. In some cases the composition is provided as a coating to a surface of the substrate of an implantable medical device such as a urological medical device.

In another embodiment, a method comprises a step of providing a composition comprising (a) a polymeric material and (b) an inhibitor of urine component crystallization, a first polymer, and an optional second polymer, wherein the second polymer modulates release of the inhibitor of urine component crystallization from the coating. The coating is then treated to provide an immobilized coating on the surface of a substrate of a medical device. In some embodiments, the composition is provided to a surface of the substrate of an implantable medical device such as a urological medical device.

The step of forming of the layers of the coating composition comprising the crystallization inhibitor composition can result in bonding the matrix polymers to each other, the surface of a device, or both, thereby forming the polymeric matrix having immobilized coatings.

Coatings can be disposed on the surface of the substrate by methods known in the art. These methods include dipping, spraying, brushing etc. the composition onto to the surface. Coatings of the composition may be formed in layers, may contain one or several inhibitors of urine component crystallization that may be the same or different, therapeutic or other agents, and may contain no crystallization or therapeutic agents in order to modulate delivery of underlying coating layers that do contain inhibitors of urine component crystallization or other agents. Coating layers may be continuous or discontinuous on the surface of the substrate of the medical device. Thickness of the coatings comprising the crystallization inhibitor composition can be at least, 5, 10, 15, 20, 30, 40, 50, 60, 70, 80, 90 or at least 100 microns on the surface of the substrate. In other embodiments the thickness of the coatings can be in a range of about 1 to about 10 um, about 10 to about 25 um, or about 25 to about 100 um, for example.

An embodiment also provides a method for localized, sustained release delivery of an inhibitor of urine component crystallization. The method comprises a step of placing or forming in a subject a crystallization inhibitor composition. In some embodiments the crystallization inhibitor composition is immobilized in a matrix of polymeric material. The crystallization inhibitor composition releases an inhibitor of urine component crystallization to minimize, reduce or prevent encrustation over an extended period of time. In some aspects, the crystallization inhibitor composition can release an inhibitor of urine component crystallization to minimize, reduce or prevent biofilm formation at or near the urological implant. In some aspects, an inhibitor of urine component crystallization is released from a coating or a microparticle on the surface of the substrate of a medical device. In some aspects an antimicrobial agent is released from a coating on the surface of the substrate of a medical device.

The composition can optionally include one or more sets of other microparticles (e.g., a second set, also referred to herein as a distinct population) or coating layers that include an inhibitor of urine component crystallization that is different than the biofilm inhibitor. For example, inventive crystallization inhibitor compositions can also be used to concurrently deliver a second, third or more inhibitors of urine component crystallization. In some aspects, the second inhibitor of urine component crystallization can be an inhibitor that has little or no solubility in water. From this standpoint, the crystallization inhibitor composition (which may be provided as a polymer matrix) is particularly advantageous as multiple types of inhibitors having different solubility characteristics can be delivered from the same composition, both inhibitors being released in a sustained manner, and generally within their respective therapeutic windows. This arrangement can provide many benefits to a subject, particularly when the presence of the two inhibitors of urine component crystallization results in an improvement over administration of one inhibitor, such as might be observed with an additive or synergistic effect.

An embodiment also provides a coating having specific inhibitor of urine component crystallization release profiles. Accordingly, in yet other aspects, a medical device having a inhibitor-releasing coating wherein at least 10, 20, 30, 40, or 50% of the inhibitor of urine component crystallization present in the coating is released within a period of 1 to 27 days. The release of inhibitor can be determined by the methods as discussed herein. In more specific cases, 50% of the inhibitor of urine component crystallization present in the coating is released within a period of 3 to 15 days, 5 to 13 days, or 7 to 111 days.

Crystallization inhibitor compositions (such as, for example, citric acid or osteopontin releasing compositions) can include (for example, 0.05 wt % to 0.5 wt % to 1 wt % to 2 wt % to 5 wt % to 10 wt % to 25 wt % to 50 wt % to 75 wt % to 90 wt % to 95 wt % to 99 wt % to 99.5 wt % or more) of the inhibitor of urine component crystallization, combined with one or more optional supplemental agents (for example, 99.95 wt % to 99.5 wt % to 99 wt % to 90 wt % to 75 wt % to 50 wt % to 25 wt % to 10 wt % to 5 wt % to 1 wt % to 0.5 wt % to 0.05 wt % or less), based on the total weight of the composition.

Crystallization inhibitor compositions for use herein may also be provided in crystalline, amorphous, solid, polymer, copolymer, liquid or semi-liquid form, commonly in the form of layer a viscous liquid or gel. Such liquid or semi-liquid compositions are commonly employed as layers or reservoir filling materials. In addition to the inhibitor of urine component crystallization and a liquid component (such as, water, other liquids such as saline and various buffers and combinations thereof), such liquid and semi-liquid compositions may also include one or more optional supplemental agents.

Therefore, in some aspects, inventive concepts provide a crystallization inhibitor composition comprising an inhibitor of urine component crystallization in combination with, or included in, a biodegradable polymer, wherein the crystallization inhibitor composition is provided in crystalline, solid, polymer, copolymer, liquid or semi-liquid form, and wherein the composition provides controlled release of the inhibitor of urine component crystallization from the composition into a subject. The inhibitor of urine component crystallization can be provided in microparticle form.

In some aspects, inventive concepts provide a crystallization inhibitor composition comprising an inhibitor of urine component crystallization and a hydrophobic polymer, wherein the crystallization inhibitor composition is provided in crystalline, solid, polymer, copolymer, liquid or semi-liquid form, and wherein the composition provides controlled release of the inhibitor of urine component crystallization from the composition into a subject. The hydrophobic polymer can be a polyalkene homopolymer or copolymer, such as a poly(maleic acid) derivative. One illustrative poly(maleic acid) derivative is photo-poly(octadecene-alt-maleic anhydride) silane. The hydrophobic polymer can be polyisobutylene. The inhibitor of urine component crystallization can be provided in microparticle form.

In another embodiment the inhibitor of urine component crystallization, such as for example, citric acid, is combined with a diol to make a pre-polymer of citric acid and diol (PCD). The PCD is then coated on the surface of a substrate of a medical device. Useful diols have the form of $C_nH_{2n}$, wherein n=2 to about 20, polyethylene glycol (PEG)diols and aryl diols. Other diols could include biomolecules such as polysaccharides, polymers such as polyvinyl alcohol or other alcohol containing polymers, or small non-linear molecules such as pentaerythritol, or molecules with more than two alcohol groups in addition to linear diols. In an embodiment, 1,8-octanediol is a useful diol. This diol combined with citric acid can form a poly(1,8-octane-co-citrate) (POC). The pre-polymer can be heated for further crosslinking relative to the needed requirements.

In another embodiment the inhibitor of urine component crystallization, such as for example, citric acid, is combined with a diol to make a pre-polymer of citric acid and diol (PCD). The PCD is then coated on the surface of a substrate of a medical device. Useful diols have the form of $C_nH_{2n}$, wherein n=2 to about 20, polyethylene glycol (PEG)diols and aryl diols. Other diols could include biomolecules such as polysaccharides, polymers such as polyvinylalcohol or other alcohol containing polymers, or small non-linear molecules such as pentaerythritol, or molecules with more than two alcohol groups in addition to linear diols. In an embodiment, 1,8-octandiol is a useful diol. This diol combined with citric acid can form a poly(1,8-octane-co-citrate) (POC). The pre-polymer can be heated for further crosslinking relative to the needed requirements.

In another embodiment a pre-polymer of the inhibitor of urine component crystallization, such as for example, citric acid, the citric acid and diol (PCD) being combined with a binder polymer that is adhesive to the surface of a substrate of a medical device and the binder and citric acid polymer is coated in the surface of the medical device. Characteristics of useful binders after combining with PCD are non-tackiness, clarity, no delamination, and adherence to the surface of the substrate. A non-limiting list of useful binder polymers are poly(4-vinylphenol-co-methyl methacrylate), poly (butyl methacrylate), poly(isobutylmethacrylate), poly(vinylbutyral) MW 180K, ethylcellulose, and poly(2-ethyl-2-oxazoline) MW50K. The binder to PCD ratio may be 1:1 to 3:1. Binder and PCD may be used with or without a primer layer. Such a primer layer is useful to increase adhesion to the substrate for other coating layers. A useful primer layer is Photo-POMAS isopropanol, (photo-poly(octadecene-alt-maleic anhydride)silane) prepared as described in Example 1 of US Publication No. 2012/0258313 A1, "Coating Agents and Coated Articles," Wen et al., 11 Oct. 2012.

In another embodiment, the inhibitor of urine component crystallization, such as for example, citric acid, the citric acid being combined with a binder polymer that is adhesive to the surface of a substrate of a medical device and the binder and citric acid is coated in the surface of the medical device. Binder and inhibitor may be used with or without a primer layer. Such a primer layer is useful to increase adhesion to the substrate for other coating layers. A useful primer layer is Photo-POMAS isopropanol, (photo-poly (octadecene-alt-maleic anhydride)silane) prepared as described in Example 1 of US Publication No. 2012/0258313 A1, "Coating Agents and Coated Articles," Wen et al., 11 Oct. 2012.

In another aspect, the pre-polymer of citric acid can be coated on the surface of the substrate of a medical device with or without a primer layer. Such a primer layer is useful to increase adhesion to the substrate for other coating layers. A useful primer layer is Photo-POMAS isopropanol, (photo-poly(octadecene-alt-maleic anhydride)silane) prepared as described in Example 1 of US Publication No. 2012/0258313 A1, "Coating Agents and Coated Articles," Wen et al., 11 Oct. 2012.

In one aspect, the pre-polymer of citric acid can be combined with PLGA or other biodegradable polymer and formed into a coating composition or a microparticle for application to a surface of a substrate of a medical device.

Examples of optional supplemental agents may be included in the coating layers or microparticles. Such agents include blending agents, imaging agents, corticosteroids, narcotic and non-narcotic analgesics, local anesthetic agents and therapeutic agents such as anti-inflammatory, antibiotics, antimicrobial, antiseptic, and other agents to combat infection.

Non-limiting examples of said therapeutic agents include natural product extracts shown to be active, such as cranberry and blueberry; tetracycline, chlortetracycline, bacitracin, neomycin, polymyxin, gramicidin, cephalexin, oxytetracycline, chloramphenicol, rifampicin, ciprofloxacin, tobramycin, gentamycin, erythromycin, penicillin, sulfonamides, sulfadiazine, sulfacetamide, sulfamethizole, sulfisoxazole, nitrofurazone, sodium propionate, minocycline, doxycycline, vancomycin, kanamycin, cephalosporins such as cephalothin, cephapirin, cefazolin, cephalexin, cephardine, cefadroxil, cefamandole, cefoxitin, cefaclor, cefuroxime, cefonicid, ceforanide, cefitaxime, moxalactam, cetizoxime, ceftriaxone, cefoperazone), geldanamycin, chlorhexidine, moxifloxacin and analogues, mixtures and blends thereof.

Examples of blending agents include suitable members of the following, among others: sugars, including sucrose, dextrose and so forth, polysaccharides including celluloses, for example, ionic celluloses such as sodium carboxymethyl cellulose, and non-ionic celluloses, for example, hydroxyalkyl celluloses such as hydroxymethyl cellulose, hydroxyethyl cellulose, and hydroxyproyl cellulose (e.g., Klucel® G and Klucel® E), further polysaccharides including alginic acid, pectinic acid, dextran, carboxymethyl dextran, modified dextran, starch, carboxymethyl starch, and additional polymers including polyethylene glycol, polyethylene terephthalate glycol (PETG), polyalkylene oxides including polyethylene oxide and polypropylene oxide, poly(acrylic acid), poly(methacrylic acid), polyvinyl alcohol, polyvinylpyrrolidone, polyacrylamide, poly(N-alkylacrylamides), poly(vinyl sulfonic acid), polyester amides, polyanhydrides, polyorthoesters, polyesters such as poly(lactide), poly(glycolide) and poly(lactide-co-glycolide), polyphosphazenes, poly(methyl methacrylate), poly(caprolactone), poly(dioxanone), poly(trimethylene carbonate), poly(methylene-bisacrylamide), proteins and polypeptides (e.g., polyglutamic acid, polylysine, etc.), suitable polymers from the above list of polymers for forming medical device substrates, as well as salts, copolymers and blends of the forgoing. In some embodiments, soluble or biodegradable blending agents are useful.

Examples of imaging agents include (a) contrast agents for use in connection with x-ray fluoroscopy, including metals, metal salts and oxides (particularly bismuth salts and oxides), and iodinated compounds, among others, (b) contrast agents for use in conjunction with ultrasound imaging, including inorganic and organic echogenic particles (i.e., particles that result in an increase in the reflected ultrasonic energy) or inorganic and organic echolucent particles (i.e., particles that result in a decrease in the reflected ultrasonic energy), and (c) contrast agents for use in conjunction with magnetic resonance imaging (MRI), including contrast agents that contain elements with relatively large magnetic moment such as Gd(III), Mn(II), Fe(III) and compounds (including chelates) containing the same, such as gadolinium ion chelated with diethylenetriaminepentaacetic acid.

In some embodiments, the crystallization inhibitor compositions may be ionically crosslinked or covalently crosslinked (for example, via biodegradable bonds, such as ester bonds formed from the hydroxyl and carboxyl groups). In some embodiments, the inhibitor of urine component crystallization within the sustained release compositions is neither ionically nor covalently crosslinked. In some embodiments, a portion of the inhibitor of urine component crystallization is un-crosslinked for more immediate release and a portion of the inhibitor is ionically or covalently crosslinked for more delayed release.

In another embodiment, the crystallization inhibitor composition is deposited as a separate layer and a topcoat of polymer is deposited, through which the inhibitor of urine component crystallization can diffuse over time. In some embodiments, that topcoat polymer is hydrophobic polymer, more particularly comprising polyalkenes, such as, for example, polyisobutylene, and copolymers thereof. Another hydrophobic polymer suitable in the topcoat layer is a poly(maleic acid) anhydride, such as photo-poly(octadecene-alt-maleic anhydride) silane. In some embodiments the topcoat layer can provide other functionality such as passivation, hemocompatiblity, or lubricity such as a hydrogel.

Other reagents may be optionally applied to the surface of the substrate to provide other functionality such as increased adhesion, for example. Suitable optional reagents can be selected to be biocompatible with the subject and to not substantially affect the controlled release of the inhibitor of urine component crystallization.

In another embodiment, the crystallization inhibitor composition is deposited as a blend of polymers through which the inhibitor of urine component crystallization may release over time.

In some embodiments, two or more inhibitors of urine component crystallization may be released from the same substrate. For example, such embodiments can be particularly useful in instances where one inhibitor is effective with one calcium salt and a separate inhibitor is effective for a different calcium salt or magnesium salt. In some embodiments two or more inhibitors of urine component crystallization could work cooperatively, synergistically, to delay crystallization and/or subsequent encrustation.

In some embodiments, medical devices can comprise one or more reservoirs. The one or more reservoirs may be, for example, formed in the surface of a substrate or may be internal to the medical device with one or more passageways extending from the reservoir to the surface of the device to allow elution of the inhibitor of urine component crystallization from within the device. Examples of reservoirs formed in the surface of a substrate surface (also referred to herein as "surface reservoirs") include depressions such as trenches, blind holes and pores, among others. Surface reservoirs may be created in a great variety of shapes and sizes. Multiple surface reservoirs can be provided in a near infinite variety of arrays. Examples of blind holes include those whose lateral dimensions at the surface are circular, polygonal (e.g., triangular, quadrilateral, penta-lateral, etc.), as well as blind holes of various other regular and irregular shapes and sizes. Trenches include simple linear trenches, wavy trenches, trenches formed from linear segments whose direction undergoes an angular change (e.g., zigzag trenches), and linear trench networks intersecting various angles, as well as other regular and irregular trench configurations. The surface reservoirs can be of any suitable size. For example, the medical devices typically contain surface reservoirs whose smallest lateral dimension (for example, the width) is less than 500 μm (micrometers), for example, ranging from 500 micrometers to 200 micrometers to 100 micrometers to 10 micrometers to 1 micrometer or less.

In other embodiments, the medical device comprises one or more internal reservoirs that are internal to the medical device with one or more passageways extending from the reservoir to the surface of the device.

For example, the medical device may comprise a substrate with an internal lumen (which may be in addition to one or more other lumens, such as drainage lumens, working channels, and the like) with access to the exterior of the device (for example, via one or more pores, holes, slots, and the like). One or more larger holes with plugs may also be provided, for example, in order to load the device with one or more types of crystallization inhibitor releasing compositions (such as liquids, gels, particles, rods, and the like). Such internal lumens may extend partially or entirely through the device. Where the lumen extends entirely through the device, plugs may be provided at each end.

As indicated above, the medical devices are urological medical devices, including any medical device that is suitable for placement in the urinary system of a subject, including the kidneys (e.g., in the renal calyx, renal pelvis, etc.), as well as the urinary tract, including ureters, urinary bladder and urethra. These include elongated devices, including elongated devices having any of a variety of solid and hollow cross-sections (for example, single lumen, multi-lumen, rod-shaped devices) including those with overall cross-sections that are circular, oval, triangular, and rectangular in shape, among many other regular and irregular overall cross-sections. Specific examples include urological stents, for example, urethral and ureteral stents, urological catheters (for example, drainage catheters, guide catheters, and the like), guidewires, urological scopes (such as cytoscopes, ureteroscopes, nephroscopes, and the like), tissue engineering scaffolds, grafts and patches, among others.

In some embodiments, devices may be employed that take on a particular beneficial shape in vivo, for example, immediately upon removal of a guide wire or emergence from a channel (for example, due to elastic rebound of the material) or upon application of an external stimulus such as heat or light (for example, where a shape memory material such as a shape memory polymer is employed). For example, the device may take on a non-linear form such as a coiled configuration. Such constructions allow the medical device to be held in place in the urinary tract, for example, by forming a coil or other retention element in the kidney (for example, in the renal calyx and/or renal pelvis), the bladder, or both. In other embodiments, the devices may comprise a balloon element that can be inflated to hold the device in place.

Several embodiments will now be described with regard to ureteral or urethral stents, although it should be understood that the embodiments of the application are not so limited.

EXAMPLES

Materials and Methods

Unless otherwise noted, chemicals were purchased through Sigma-Aldrich, Milwaukee, Wis., and used as received. "Photoreactive poly(vinylpyrrolidone) (photo-PVP)" used herein was prepared as described in U.S. Pat. No. 8,679,454 (Guire et al.). NMR was performed on a 300 MHz Varian NMR through the University of Minnesota's Dept of Chemistry service. UV Illumination was performed using a Harland Medical Systems UVM400 lamp (Harland Medical Systems, Eden Prairie, Minn.), under conditions noted for each procedure.

Poly(Diol-Citrate) Synthesis of Pre-Polymers

Equimolar amounts of citric acid and 1,8-octanediol (98%) were added to a 250-mL round-bottom flask with stirbar. The reactants were melted by placing the flask into a 155° C. oil bath for 5 minutes with stirring. After 5 minutes, the temperature was lowered to 140° C. The reagents were allowed to react for 30 minutes and then the flask was removed from the oil bath to let cool. The pre-polymer was allowed to cool for 30 minutes to 1 hour before approximately 80 mL of acetone was added to facilitate transfer to 10 20-mL scintillation vials. Acetone was removed from the pre-polymer/acetone solution by rotary evaporation. Product was poly(citrate-co-1,8-octanediol) (POC). Similar synthetic methods were used to prepare pre-polymers using 1,3-propanediol and 1,6-hexanediol in lieu of 1,8-octanediol. As used herein, "pre-polymer" refers to copolymers that have not been cross-linked.

Optimized Pre-Polymer Cross-Linking Conditions for Poly (Citrate-Co-1,8-Octanediol) (POC)

Scintillation vials containing POC pre-polymer were covered with a Kimwipe and incubated at 60° C. without vacuum for 2.25-2.5 days. Other conditions included cross-linking pre-polymer at 100° C. under vacuum approximately 28 torr) for 1-7 days.

Flat Substrate Coating Procedure

Approximately 40 mg of POC crosslinked polymer was placed onto a flat polyurethane (PU) substrate of approximately 5.5 cm×2.0 cm using POC/IPA solutions of various concentrations. The solvent was allowed to evaporate overnight at room temperature.

Rod Substrate Coating Procedure

POC coating solutions (30, 50, and 70 mg/mL) in IPA were used for dip-coating PU rods, resulting in a coating mass of approximately 1.5 mg. A dwell time of 30 seconds and a coating speed of either 0.5 or 0.775 cm/sec was used.

Velcro Adhesion Test

Flat substrates were placed into an apparatus that used a 329-g weight on top of a soft piece of Velcro to test coating adhesion to the PU substrate. The substrate was weighed and imaged before and after this test to determine if any coating mass was lost during the testing. The substrate was pulled through five times dry and the new mass was recorded. The substrate was then pulled through the apparatus five more times after the surface was wet with DI water and let dry at least overnight at room temperature before its new mass was recorded.

Elution of Citric Acid Coatings

To determine the amount of citric acid released by both flat and rod coated substrates, substrates were placed in either 10 or 20 mL of 1×-10×PBS or purified water for 19 to 30 days. The buffer or water was changed after approximately 1 hour, 1 day, 3 or 4 days, 7 days, 2 weeks, 3 weeks, and 4 weeks/30 days. Citric acid was quantified using a Citric Acid Assay Kit (Sigma Aldrich MAK057) following the manufacturer's instructions.

Preparation of Osteopontin Loaded PLGA Particles

A 100-mg aliquot of PLGA (poly(lactic-co-glycolic acid), 50:50, MW 40,000-75,000), was dissolved by vortexing in 1 mL dichloromethane. To the polymer solution, 100 µL of 50 µg/mL of osteopontin (human osteopontin, R&D Systems, Minneapolis, Minn.) in deionized water was mixed and dispersed by probe sonication for 30 seconds. A 4-mL aliquot of 1% (w/v) aqueous poly(vinylalcohol) (PVA) was added to the drug suspension and emulsified by homogenization for 30 seconds. The resultant oil-in-water (O/W) emulsion was poured into 30 mL of 0.3% (w/v) PVA solution and stirred overnight at room temperature. After evaporation of the organic solvent, the hardened microparticles were collected by centrifugation at 1500 rpm for 10 minutes, washed three times with 5 mL deionized water, lyophilized and stored under desiccation at −20° C. The same procedure, minus the osteopontin, was used for the empty PLGA particle control.

Coating with Osteopontin-Loaded PLGA Particles on Parylene™-Treated Stainless Steel Discs (Elution, Encrustation, and Tape Test)

Parylene™ treated stainless steel discs (8.00 mm diameter by 0.56 mm thick, V&P Scientific, Inc. San Diego, Calif.) were cleaned with isopropanol. Then, 100 µl of 2.5 mg/mL photoreactive poly(vinlypyrrolidone) in isopropanol solution was spread out on each disc. After solvent evaporation, each disc was irradiated with ultraviolet light (250 nm to 450 nm) for 3 minutes (Harland Medical UVM400, MN, distance from light source was 8 inches).

A suspension of 6 mg osteopontin-loaded microparticles (or empty microparticles) in 100 µl of 2.5 mg/mL photoreactive poly(vinlypyrrolidone) in aqueous solution was then added on top of the poly(vinylpyrrolidone) coating. After drying at room temperature for 4 h, each disc was UV irradiated under conditions noted above in this Example.

Finally a topcoat of photoreactive poly(vinylpyrrolidone) was applied on top of the immobilized microparticles by adding 100 µl of 2.5 mg/mL photoreactive polymer/isopropanol solution. The discs were again subjected to irradiation with UV light as described above in this Example. The coated discs were stored under desiccation at −20° C.

Osteopontin Elution Assay

To determine the amount of osteopontin released, coated Parylene™ coated discs were placed in 2 mL of 1×PBS for up to 30 days. The buffer was exchanged at approximately 30 minutes, 1 hour, 1 day, 5 days, 10 days, 15 days, and 30 days. Eluted samples were refrigerated until assaying. Osteopontin was quantified using an Osteopontin ELISA kit (R &D Systems, Mpls, MN) following the kit's instructions.

Preparation of Citric Acid Loaded PLGA Particles

A 100-mg aliquot of PLGA (50:50, MW 40,000-75,000) was dissolved by vortexing in 1 mL dichloromethane. To the polymer solution, 100 µL of 0.06 mg/ml citric acid prepolymer solution in deionized water was mixed and dispersed by probe sonication for 30 seconds. A 4-mL aliquot of 1% (w/v) aqueous poly(vinylalcohol) (PVA) was added to the drug suspension, and the resulting mixture was emulsified by homogenization for 30 seconds. The resultant oil-in-water (O/W) emulsion was poured into 30 mL of 0.3% (w/v) PVA solution and stirred overnight at room temperature. After evaporation of the organic solvent, the hardened microparticles were collected by centrifugation at 1500 rpm for 10 minutes, washed three times with 5 mL deionized water adjusted to pH 7, lyophilized and stored under desiccation at −20° C.

Coating with Citric Acid PLGA Particles on Polyurethane Flat Samples for Adhesion Testing Flat polyurethane substrates (2.5 cm×7.5 cm, McMaster Carr) were cleaned with isopropanol wipes and then air dried. A 1.0-ml aliquot of a 2.5 mg/ml photoreactive PVP solution in isopropanol was added to the solution by pipet over an approximately 3 cm² area and allowed to air dry. After drying, the samples were UV illuminated for 3 minutes with 254 nm light. To the samples, 2.0 ml of a suspension of 500 mg citric acid PLGA particles (5% loading level) in 2.5 mg/ml photoreactive PVP in isopropanol was added via pipette and air dried for at least 24 hours and then illuminated for 3 minutes with 254 nm light (Harland UVM400).

Two final coats of 1 ml of 2.5 mg/ml aqueous photoreactive PVP and then 10 mg/ml photoreactive PVP were applied, with air drying and illumination for 3 minutes with 254 nm light (Harland UVM400) after application of each coat.

Tape Test (ASTM D 3359 Method B) for PLGA Coatings on Parylene™-Treated Discs

Figure 2:
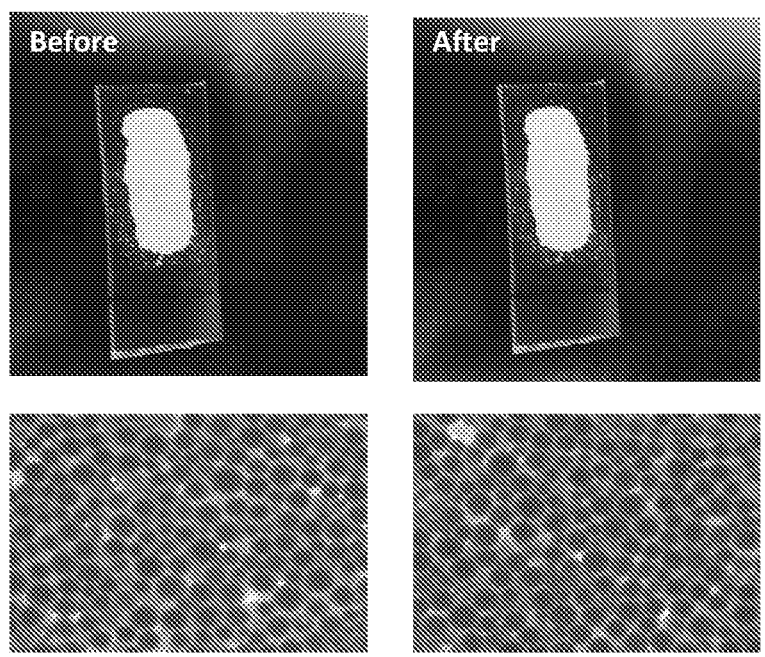
FIG. 2 shows crystallization inhibitor coatings before and after friction testing. Lower images are at 400× magnification.

Nine coated Parylene™ treated discs were weighed, and then Scotch Magic Tape was briefly applied to each coated surface and smoothed with moderate pressure. After approximately 2 minutes, the tape was peeled back at 180° and removed from each disc in approximately 2 seconds. Coatings with at least an 80% survival rate were considered durable. The discs were re-weighed to determine weight loss Friction Test for PLGA Coatings on Polyurethane Flat Samples Citric acid PLGA coatings were first weighed and imaged, and the coating durability was challenged on an FTS5001 friction tester (Harland Medical Systems, Eden Prairie, Minn.), with 300 grams normal force against Teflon pads. The samples were pulled upward for 2.5 cm with a velocity of 2 cm/sec against the Teflon surface, then the normal force was released and the samples were moved back down to the starting position. The samples were tested over five cycles, then reweighed and imaged to determine coating loss. Imaging was performed at 400× shown in FIG. 2.

Cytotoxicity

Samples were soaked in Dulbecco's Modified Eagle's Medium (DMEM), 10% fetal bovine serum for 72 hours at 37° C. Then, that extraction media was added to confluent human dermal fibroblast cells (ATCC® PCS-201-010, passage 2), and the cells were incubated in it overnight. The cells were imaged with LIVE/DEAD® staining to determine viability.

Encrustation Assay

Artificial urine solutions contained either:

A (Solution 2) An aqueous solution of sodium hydrogen phosphate (48 mM), urea (26.6 mM), calcium chloride (9.1 mM), and disodium oxalate (3 mM), pH 6; or B (Solutions A & B) An aqueous solution of 0.825 g/L calcium chloride dehydrate, 2.272 g/L sodium sulfate, 0.534 g/L magnesium sulfate heptahydrate, 2.086 g/L ammonium chloride, 5.668 g/L potassium chloride, 3.178 g/L sodium hydrogen phosphate monobasic, 0.406 g/L sodium hydrogen phosphate dibasic, 0.546 g/L tri sodium citrate dehydrate, 6.330 g/L sodium chloride, 0.943 g/L calcium chloride, and 0.375 g/L disodium oxalate, pH 6.

Sample discs of 1 cm² (polyurethane or Parylene™ coated stainless steel) were placed in 2 ml of artificial urine solution in a 20-ml scintillation vial at 37° C. with orbital shaking at 50 rpm for 5 weeks. Both samples and the scintillation vial were cleaned with IPA prior to use. The artificial urine samples were filtered with a 0.22-μm filter prior to use. If the encrustation assay used *Proteus mirabilis* (ATCC® 7002), 5 ml of artificial urine was used per disc in addition to 500 milliliter of bacterial suspension ($2.5 \times 10^9$ CFU/mL stock). Larger polyurethane rod samples were placed in 10 mL of artificial urine.

After 5 weeks' incubation, the samples were removed from the artificial urine solution, rinsed with deionized water, then shaken vigorously overnight at room temperature in 2 mL (5 mL for larger pieces) of 1.0 M HCl to dissolve the encrustation, and sonicated for 1 hour. The resulting solutions were neutralized to pH 7.0 with sodium hydroxide, and then colorimetric assays for calcium and/or magnesium were performed following manufacturer's procedures (Sigma Aldrich, St. Louis, Mo.).

Example 1. Osteopontin PLGA Coatings

The sialoprotein osteopontin was encapsulated in PLGA microparticles as described above ("Preparation of Osteopontin Loaded PLGA particles"). Microparticles were prepared at two theoretical loading levels, 0.05% and 0.2% by weight. Loaded microparticles were then crosslinked in a photoreactive hydrogel coating as described above ("Coating with Osteopontin-Loaded PLGA particles on Parylene™-coated stainless steel discs"). The microparticles could be stably immobilized with the method above in the photoreactive hydrogel coated onto Parylene™-coated discs. The opaque white coatings were durable to touch.

Sample discs coated with either osteopontin loaded PLGA coatings or empty PLGA coatings were placed in 1×PBS for elution over 30 days at 37° C., with the elution buffer exchanged at days 1, 5, 10, 15, and 30.

Osteopontin release was quantified by an ELISA kit (R&D Systems) and shown in FIG. 1. As the elution progressed, osteopontin was released over the entire 30-day period. Total release per disc was 0.3 ng osteopontin released over 30 days (6-mg PLGA coating/3 ng osteopontin loading per disc). See FIG. 1.

The durability of these coatings was then investigated and demonstrated by the tape test and friction test. As noted above, tape tests used an industry standard, ASTM D 3359. As shown in Table 1, the coatings did not delaminate visibly nor was there coating material visible on the removed tape. As noted in the Table 1, there was very little measurable weight loss (representing about less than 20 or 25 wt. %) of the coating following the tape test.

TABLE 1

Durability Results for PLGA hydrogel coatings.

| Coating | Tape Test on parylene discs | | Friction Test on polyurethane flat | |
| --- | --- | --- | --- | --- |
| | Visible loss? Y/N | Weight Loss | Visible loss? Y/N | Weight Loss |
| PLGA Empty, no loading | No | 0.14% weight loss | — | — |
| PLGA osteopontin loaded | No | 0% weight loss | — | — |

TABLE 1-continued

Durability Results for PLGA hydrogel coatings.

| Coating | Tape Test on parylene discs | | Friction Test on polyurethane flat | |
| --- | --- | --- | --- | --- |
| | Visible loss? Y/N | Weight Loss | Visible loss? Y/N | Weight Loss |
| PLGA Citric acid loaded | No | 0% weight loss | No loss | 0.92% weight loss |

Friction testing (Harland Medical FTS5001 friction tester) showed no visible change or weight loss over a much larger surface area and coating weight (coating weight was 130 mg per sample). The results were consistent among coatings that were made from both empty and loaded PLGA microspheres and not dependent on the loaded active agent. These results show uniform, durable coatings.

The coatings were analyzed for encrustation. This assay involved immersing the coated discs in an Artificial Urine Solution A for 5 weeks at 37° C., then rinsing the pieces thoroughly and dissolving off the encrustation with 1.0 M HCl. The dissolution solutions were then neutralized and tested for calcium and magnesium content by commercial colorimetric kits (Sigma Aldrich). In some experiments, the artificial urine was spiked with $2.5 \times 10^9$ CFU/ml of *Proteus mirabilis*, which is implicated in stent encrustation. *P. mirabilis* excretes a particularly active urease, which in urine will split urea to give ammonia, thus increasing pH and subsequent encrustation.

Results, shown in Table 2, give a clear indication that the osteopontin reduced encrustation. The coating alone without the osteopontin also may reduce encrustation, though it was not statistically significant in this experiment. PLGA by itself might be expected to reduce encrustation because it releases acid as it biodegrades, which in this case, would act as a complementary mechanism for reducing encrustation and possibly a secondary crystallization inhibitor.

TABLE 2

Encrustation Results for Osteopontin Coatings

| Coating | Ca + 2 content* | % Reduction |
| --- | --- | --- |
| Uncoated parylene disc | 31.7 ± 2.8 μg/ml | — |
| Empty PLGA hydrogel coating on parylene disc | 28.6 ± 2.3 μg/ml | — |
| Osteopontin- loaded PLGA hydrogel coating on parylene disc | 21.2 ± 0.8 μg/ml | 33% reduction vs. UC parylene 26% reduction vs Empty PLGA |

*Calcium content in 1.0M HCl solutions used to dissolve encrustation off pieces, n = 3 osteopontin loaded discs. Experiment was performed with artificial urine A, without *P. mirabilis* for five weeks' incubation at 37° C.

Example 2: Citric Acid Releasing Coatings

In this Example, the copolymer was made by combining citric acid and octanediol in a 1:1 molar ratio and heating neat at 140° C. for at least 30 minutes. The resulting pre-polymer was approximately 1000 molecular weight and could be further crosslinked under heat and vacuum to give the desired mechanical and citric acid release properties.

The pre-polymer was used in two ways to formulate citric acid releasing coatings: as an additive to the PLGA microsphere hydrogel coatings described above (in place of osteopontin) and as a stand-alone coating with further crosslinking.

Citric Acid Loaded PLGA Microsphere Hydrogel Coatings

PLGA microspheres were loaded at 5 and 10 wt % with a pre-polymer synthesized from 1:1 molar citric acid: 1,8-octanediol. The 5% loading level gave uniformly spherical and discrete microspheres and 5% was used in all subsequent experiments. The hydrogel coating was prepared with these citric acid copolymer-loaded PLGA microspheres in the same manner as the osteopontin-loaded PLGA microspheres except that the coating was applied to polyurethane rods and flats as well as Parylene™-coated discs. It was expected that there would be no change in durability and uniformity, and Table 3 confirms that assumption.

Elution experiments were performed with the citric acid-loaded PLGA hydrogel coatings on polyurethane over 30 days at 37° C. into 1×PBS, then the citric acid was quantified by an enzymatic colorimetric kit. Results showed excellent elution over the full period. The polyurethane controls showed decreasing citric acid activity over time, which could be due to leaching of an additive in the polyurethane that may have interfered with the assay.

Figure 3:
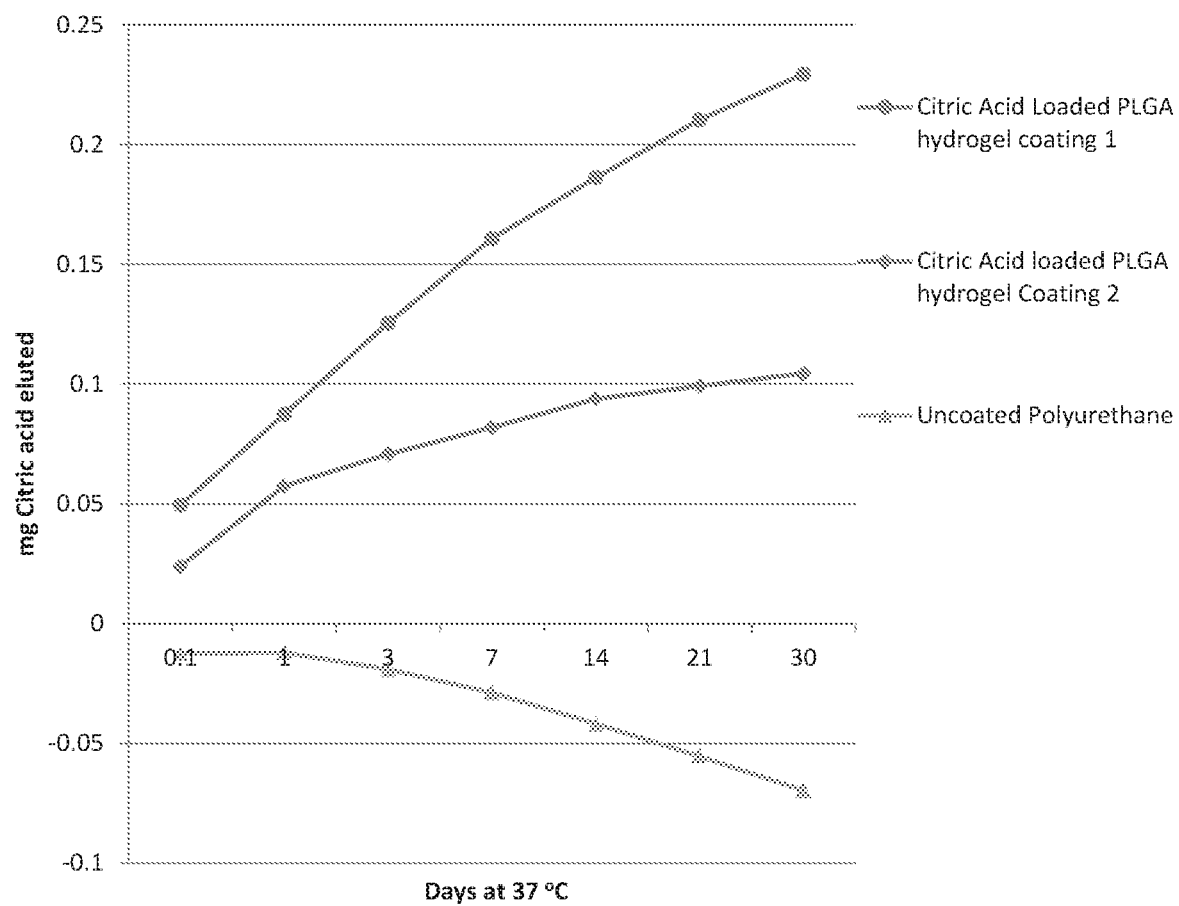
FIG. 3 illustrates crystallization inhibitor release from prepolymer loaded coatings. The two coatings had different surface area and weights.

Encrustation experiments were also performed, showing similarly positive results in Table 3. The results reported are two separate experiments with and without *P. mirabilis* spiked into the artificial urine. The first experiment was on Parylene™-coated discs, while the second was on polyurethane rods. The second also used Artificial Urine Solution B instead of Artificial Urine Solution A. The spiking was done at $10^8$ CFU/ml which represents a large non-representative bacterial load (i.e., much larger than would be typically be present in the human body). Once again the citric acid performed well compared to uncoated (up to 66% reduction), as well as to the control empty PLGA (coating minus the citric acid copolymer), with a reduction of 26-48%, see FIG. 3.

TABLE 3

Encrustation Assay of Citric acid loaded PLGA hydrogel coatings with and without *P. mirabilis* present.

| Coating | Ca + 2 content *P. mirabilis* present | Ca + 2 content no bacteria | % Reduction |
|---|---|---|---|
| Empty PLGA hydrogel coating on parylene disc | 0.27 g/l | 0.19 g/l | — |
| Citric acid loaded PLGA hydrogel coating on parylene | 0.25 g/l | 0.097 g/l | 48% |
| Uncoated polyurethane | — | 0.92 g/l | — |
| Empty PLGA hydrogel coating on polyurethane rod | 0.54 g/l | 0.43 g/l | — |
| Citric acid loaded PLGA hydrogel coating on polyurethane rod | 0.51 g/l | 0.32 g/l | 26% vs. PLGA control 66% vs Uncoated PU |

Example 3. Synthesis and Cross-Linking Citric Acid Pre-Polymers

To reduce complexity and increase loading levels over the citric acid PLGA method, we synthesized and further investigated crosslinked citric acid copolymer coatings by themselves as well as coated directly on polyurethane (PU) flats and rods.

Various reaction conditions for further crosslinking of the synthesized propanediol (PPC), hexanediol (PHC), and octanediol citric acid (POC) pre-polymers were studied. Polymerization temperature, conditions with and without vacuum (28 torr), and dissolution in 1×PBS (pH 7.4) are shown in Table 4 below. The resulting crosslinked citric acid copolymer coatings were placed in 1×PBS for 25 days and dissolution was monitored visually. Use conditions were developed which maximized solubility in isopropanol (the coating solvent) while minimizing solubility in water (the elution solvent). It was found that four days of crosslinking at 60° C. without vacuum was optimal. These conditions are referred to as "Dry" in that the crosslinking is done in the dry state prior to coating. A coating solution of 30 mg/ml "Dry" crosslinked POC copolymer in isopropanol was used to coat polyurethane flats and rods.

TABLE 4

Cross-linking conditions for PPC, PHC, and POC pre-polymers and subsequent polymer dissolution observations in 1X PBS over the course of 25 days.

| Coating | Diol | Cross-linking Temperature (° C.) | Vacuum at 28 torr | Cross-linking Reaction Time (Days) | Days in 1X PBS Before Dissolution |
|---|---|---|---|---|---|
| PPC | Propane | 60 | − | 1 | 1 |
| | | 100 | + | 1 | 2 |
| | | 60 | − | 2 | 1 |
| | | 100 | + | 2 | Stable to 25 days |
| | | 60 | − | 5 | Stable to 25 days |
| | | 100 | + | 5 | Stable to 25 days |
| PHC | Hexane | 60 | − | 1 | 2 |
| | | 100 | + | 1 | Stable to 25 days |
| | | 60 | − | 3 | Stable to 25 days |
| | | 100 | + | 3 | Stable to 25 days |
| POC | Octane | 136 | + | 1 | Stable to 25 days |
| | | 100 | + | 1 | Stable to 25 days |
| | | 60 | − | 2 | Stable to 25 days |
| | | 100 | + | 2 | Stable to 25 days |

Coating Polyurethane Substrates Prior to Crosslinking

To compare whether the coatings should be cross-linked further before or after coating the polyurethane substrates, two conditions were studied for crosslinking post-coating—either 60° C. (no vacuum) or 100° C. at approximately 28 torr.

A 30-mg/mL POC pre-polymer solution (no crosslinking) in isopropanol was used to dip-coat polyurethane rod substrates. Half of the rods were incubated in an oven to further cross-link the POC at 60° C. for 4 days; these samples are referred to as "Wet 1." The other half of the coated rods were incubated at 100° C. under vacuum (approximately 28 torr) for 4 days; these samples are referred to as "Wet 2."

Figure 4:
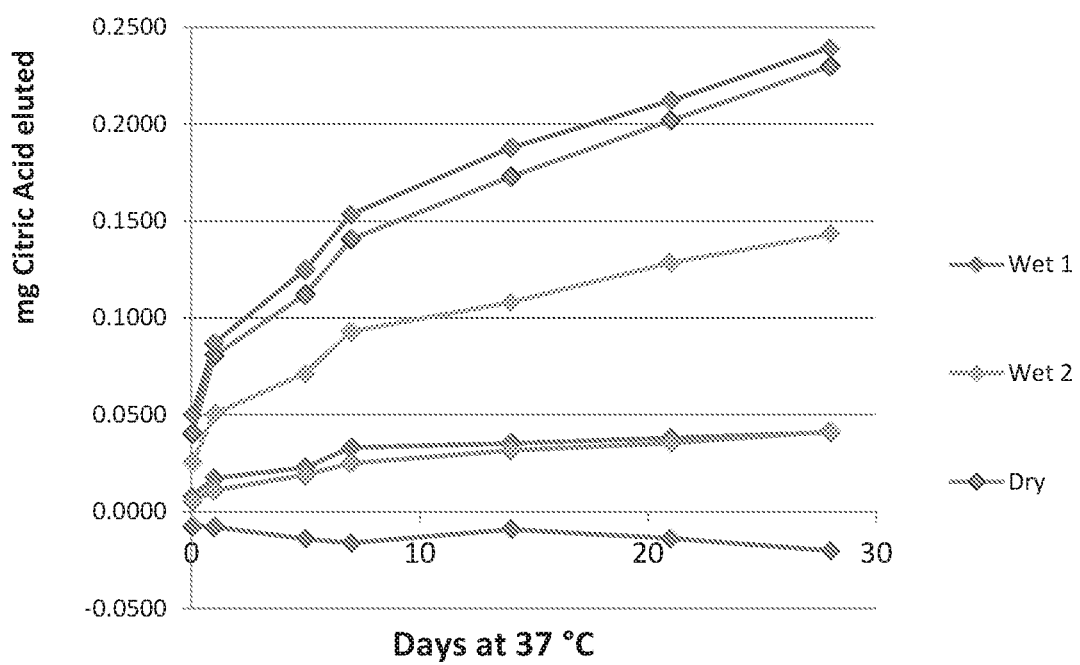
FIG. 4 shows crystallization inhibitor release from prepolymer further cross-linked on polyurethane rod substrates as well as previously crosslinked crystallization inhibitor before coating (Dry 1).

All rods were incubated in distilled water exchanged periodically over the course of 4 weeks. A colorimetric kit for quantitating citric acid was used to determine citric acid elution in distilled water from the rod substrates in accordance with the manufacturer's instructions. These results are shown in FIG. 4. There was increasing cumulative release for both substrates coated with Dry POC polymer over the course of 4 weeks.

In addition, both the Wet 1 and Dry POC coatings were analyzed for encrustation using the same procedure described previously. This assay involved immersing the coated discs in an artificial urine solution for 5 weeks at 37° C., then rinsing the pieces thoroughly and dissolving off the encrustation with 1.0 M HCl. The dissolution solutions were then neutralized and tested for calcium and magnesium content by commercial colorimetric kits (Sigma Aldrich).

TABLE 5

Encrustation Results for POC Dry and Wet 1 Coatings

| Coating | Ca + 2 content* | % Reduction |
|---|---|---|
| Uncoated polyurethane rod | 0.034 µg/µL | — |
| Wet 1 POC-coated rod | 0.012 µg/µL | 65% reduction vs. Uncoated polyurethane |
| Dry 1 POC-coated rod | 0.012 µg/well | 65% reduction vs. Uncoated polyurethane |

*Calcium content in 1.0M HCl solutions used to dissolve encrustation off pieces, Experiment was performed with artificial urine A, without P. mirabilis for five week incubation at 37° C.

Coating Concentration of Cross-Linked POC Polymer

Figure 5:
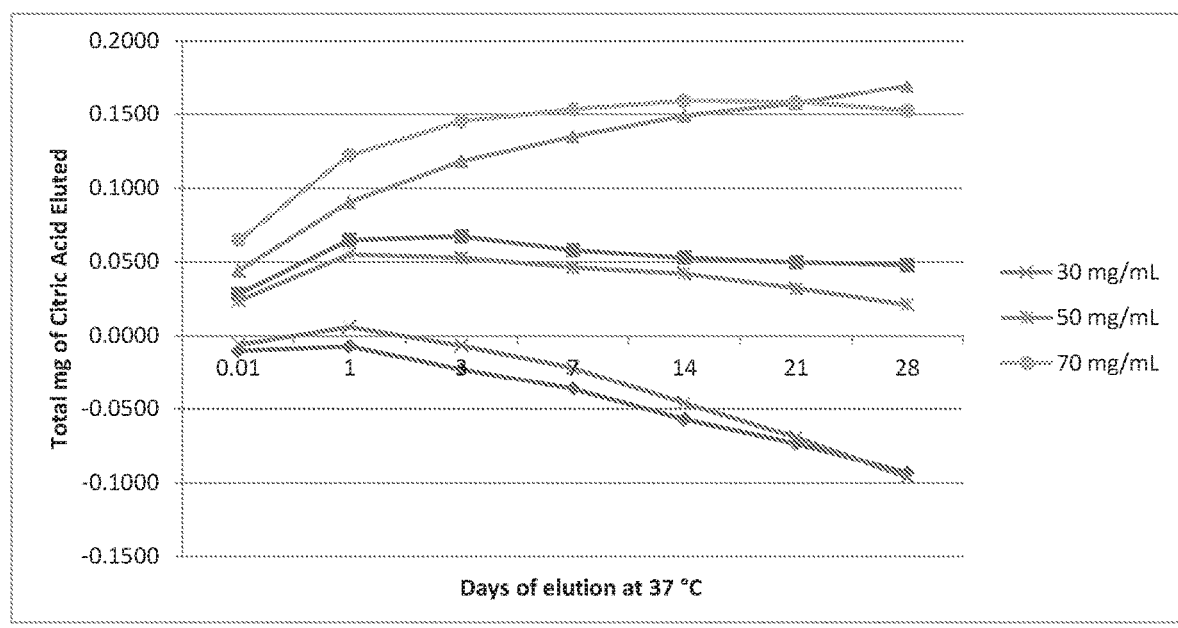
FIG. 5 illustrates crystallization inhibitor release from cross-linked "Dry" over the course of 4 weeks (672 hours).

After determining that the "Dry" POC polymer conditions worked best for dip-coating PU rods, three different concentrations of Dry POC polymer were tested in IPA: 30, 50, and 70 mg/mL. Rods were allowed to dry at room temperature overnight and were then incubated in distilled water for 4 weeks. Elution samples from each time point were tested using a Citrate Acid Test as described previously, and results are shown in FIG. 5. The 70 mg/mL POC-coated polyurethane rods showed continuous elution up to 3-4 weeks. As mentioned previously, it appears that over time the polyurethane leaches an inhibitor of the assay, causing the downward slope. As a result, citric acid was probably underestimated at longer times in this elution data. The results in FIG. 5 represent a minimum of citric acid eluted over the period.

Example 4. Three Layer Citric Acid Coating with Primer and Topcoat on Silicone Rubber A 5-inch sample of silicone rubber tubing is cleaned by isopropanol wipe three times, then air dried. A primer layer is deposited on the silicone surface by dip coating into a 30 mg/ml solution of Photo-POMAS in isopropanol, (photo-poly(octadecene-alt-maleic anhydride)silane) prepared as described in Example 1 of US Publication No. 2012/0258313 A1, "Coating Agents and Coated Articles," Wen et al., 11 Oct. 2012. The reagent is commercially available from Innovative Surface Technologies, Inc. (St. Paul, Minn.). Samples are inserted into coating solution at a rate of 2 cm/sec, dwelled in the solution for 30 seconds, and extracted from the coating solution at 0.5 cm/sec. The primer coating is air dried for 10 minutes at room temperature, then UV illuminated for one minute with 254 nm light (40 mW/cm$^2$).

An aqueous solution of citric acid is prepared by dissolving 1 gram in 10 ml of distilled water. This citric acid solution is spray coated on primer coated pieces with a low volume low pressure EFD 7856-46SS sprayhead with Valvemate 2000 (Nordson EFD, East Providence, R.I.). The silicone rubber tubing is affixed horizontally on a spinning mandrel with a spin rate of 8.5 rpm and the spray head is moved via an ExactaCoat xyz plotter (Sonotek Corp, Milton, N.Y.) at 1.5 mm/sec along the length of the tubing at a distance of 0.5 inches above the tubing. Once coated, the tubing is removed from the mandrel and air dried hanging vertically.

A solution of 30 mg/ml polyisobutylene and 10 mg/ml Photo-POMAS in hexane is prepared. Catheters coated with citric acid are dipcoated in the polyisobutylene: Photo-POMAS solution by inserting at 2 cm/sec, then immediately extracting at 0.5 cm/sec and air drying overnight at room temperature.

Example 5. Release of Osteopontin and Chlorhexidine from a Single Coating

PLGA Microparticles containing osteopontin are prepared as in Example 1. A second set of PLGA microparticles with chlorhexidine is prepared as described in Example 9 of U.S. Pat. No. 8,679,454 (Guire et al.). The two sets of microparticles are mixed together in a slurry of photoreactive polyvinylpyrrolidone at 100 mg each of the microparticle preparations with 5 mg of photoreactive polyvinylpyrrolidone in 2 ml of isopropanol. The resulting slurry could be cast onto polyurethane and air dried, then UV illuminated for 3 minutes with 254 nm light (UV fluorescent lamps, Ushio G 15T8, Ushio America, Inc. Cypress, Calif.).

What is claimed is:

1. An implantable urological device comprising a surface and a multilayer coating comprising: (a) a crystallization inhibitor composition, the crystallization inhibitor composition comprising:
   an inhibitor of urine component crystallization provided as a first coating layer on the surface, and
   (b) a permeable, hydrophobic polymer topcoat layer disposed on the first coating layer,
   wherein the inhibitor of urine component crystallization is present in an amount in a range of 60 wt % to 99.5 wt % based on total weight of the first coating layer, and
   wherein the inhibitor of urine component crystallization diffuses through the polymer topcoat to provide continuous release of the inhibitor of urine component crystallization from the surface of the device into a subject.

2. The implantable urological device of claim 1 wherein the inhibitor of urine component crystallization comprises citric acid, osteopontin or a combination of citric acid and osteopontin.

3. The implantable urological device of claim 1 wherein the inhibitor of urine component crystallization comprises an inhibitor of calcium salt or magnesium salt formation.

4. The implantable urological device of claim 1 wherein the hydrophobic polymer topcoat comprises a polyalkene homopolymer or copolymer.

5. The implantable urological device of claim 4 wherein the polyalkene homopolymer or copolymer comprises polyisobutylene.

6. The implantable urological device of claim 1 comprising a urinary catheter, ureteral stent, urethral stent, ureteral catheter, or urinary drainage system.

7. The implantable urological device of claim 1 wherein the device is fabricated of stainless steel, polyurethane, or silicone rubber.

8. The implantable urological device of claim 1 wherein the crystallization inhibitor composition further comprises a binder polymer.

9. The implantable urological device of claim 8 wherein the binder polymer comprises one or more of poly(4-vinylphenol-co-methylmethacrylate), poly(butyl methacrylate), poly(isobutylmethacrylate), poly(vinylbutyral), ethylcellulose and poly(2-ethyl-2-oxazoline).

10. The implantable urological device of claim 1 further comprising an antimicrobial agent.

11. The implantable urological device of claim 1 wherein the crystallization inhibitor composition comprises the inhibitor of urine component crystallization provided in a microparticle of biodegradable polymer.

12. The implantable urological device of claim 1 further comprising a second polymer.

13. The implantable urological device of claim 12 wherein the second polymer comprises poly(vinylpyrrolidone) or poly(acrylamide).

14. The implantable urological device of claim 1 further comprising a primer layer.

15. The implantable urological device of claim 14 wherein the primer layer comprises a poly(maleic acid) derivative.

16. The implantable urological device of claim 15 wherein the poly(maleic acid) derivative comprises photo-poly(octadecene-alt-maleic anhydride) silane.

17. An implantable urological device comprising a surface and a multilayer coating on the surface, the coating comprising:
  (a) a citric acid coating layer; and
  (b) a permeable, hydrophobic polyalkene topcoat layer disposed on the citric acid coating layer,
  wherein the citric acid coating layer comprises citric acid in an amount in a range of 60 wt % to 99.5 wt % based on total weight of the citric acid coating layer, and
  wherein the multilayer coating provides continuous release of the citric acid from the citric acid coating layer and through the hydrophobic polyalkene topcoat into a subject.

18. The implantable urological device of claim 17 wherein the topcoat layer comprises polyisobutylene, a polymaleic acid derivative, or a combination thereof.

19. The implantable urological device of claim 17 comprising a urinary catheter, ureteral stent, urethral stent, ureteral catheter, or urinary drainage system.

20. The implantable urological device of claim 17 further comprising an antimicrobial agent.

21. The implantable urological device of claim 17 further comprising a primer coating layer.

22. The implantable urological device of claim 21 wherein the primer coating layer comprises a poly(maleic acid) derivative.

* * * * *